(12) United States Patent
Chan

(10) Patent No.: US 8,372,352 B2
(45) Date of Patent: Feb. 12, 2013

(54) BIOSENSOR ASSEMBLY WITH DRUM TYPE CONTAINER FOR ANALYTICAL ELEMENTS

(75) Inventor: Frank A. Chan, Sunnyvale, CA (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/332,458

(22) Filed: Dec. 21, 2011

(65) Prior Publication Data

US 2012/0118050 A1    May 17, 2012

Related U.S. Application Data

(62) Division of application No. 12/324,088, filed on Nov. 26, 2008, now Pat. No. 8,147,755.

(51) Int. Cl.
*G01N 31/22* (2006.01)
*G01N 33/48* (2006.01)

(52) U.S. Cl. ............ 422/404; 422/50; 422/68.1; 436/63

(58) Field of Classification Search .................... 422/404
See application file for complete search history.

(56) References Cited

U.S. PATENT DOCUMENTS

| | | | |
|---|---|---|---|
| 5,298,425 A | 3/1994 | Kuhn et al. | |
| 5,510,266 A | 4/1996 | Bonner et al. | |
| 5,632,410 A | 5/1997 | Moulton et al. | |
| 5,738,244 A | 4/1998 | Charlton et al. | |
| 6,475,436 B1 | 11/2002 | Schabbach et al. | |
| 6,497,845 B1 | 12/2002 | Sacherer | |
| 6,872,358 B2 | 3/2005 | Hagen et al. | |
| 7,138,089 B2 | 11/2006 | Aitken et al. | |
| 7,270,247 B2 | 9/2007 | Charlton | |
| 7,337,918 B2 | 3/2008 | Fowler et al. | |
| 2004/0138688 A1 | 7/2004 | Giraud | |
| 2005/0118071 A1 | 6/2005 | Sacherer | |
| 2005/0187444 A1 | 8/2005 | Hubner et al. | |
| 2006/0182656 A1 | 8/2006 | Funke et al. | |
| 2007/0009381 A1* | 1/2007 | Schulat et al. | 422/58 |
| 2007/0183925 A1 | 8/2007 | Schabbach | |
| 2007/0196240 A1 | 8/2007 | Boozer et al. | |
| 2007/0264166 A1 | 11/2007 | West et al. | |
| 2008/0089812 A1* | 4/2008 | Uehata et al. | 422/104 |

FOREIGN PATENT DOCUMENTS

| | | |
|---|---|---|
| EP | 1 574 855 A1 | 9/2005 |
| EP | 1 936 374 A1 | 6/2008 |
| JP | 2002 196003 A | 7/2002 |
| WO | WO 2006/102348 A1 | 9/1982 |

* cited by examiner

*Primary Examiner* — Jill Warden
*Assistant Examiner* — Julie Tavares
(74) *Attorney, Agent, or Firm* — Krieg Devault LLP

(57) ABSTRACT

A drum type container for analytical elements comprises a casing defining a compartment with a plurality of portions for receiving respective ones of the analytical elements. The container further comprises a base assembly to which the casing is rotatably mounted. The base assembly includes a dispenser mechanism for dispensing the glucose test strips from the casing and a locking mechanism for maintaining an alignment of a selected one of the compartment portions with the dispensing mechanism.

20 Claims, 4 Drawing Sheets

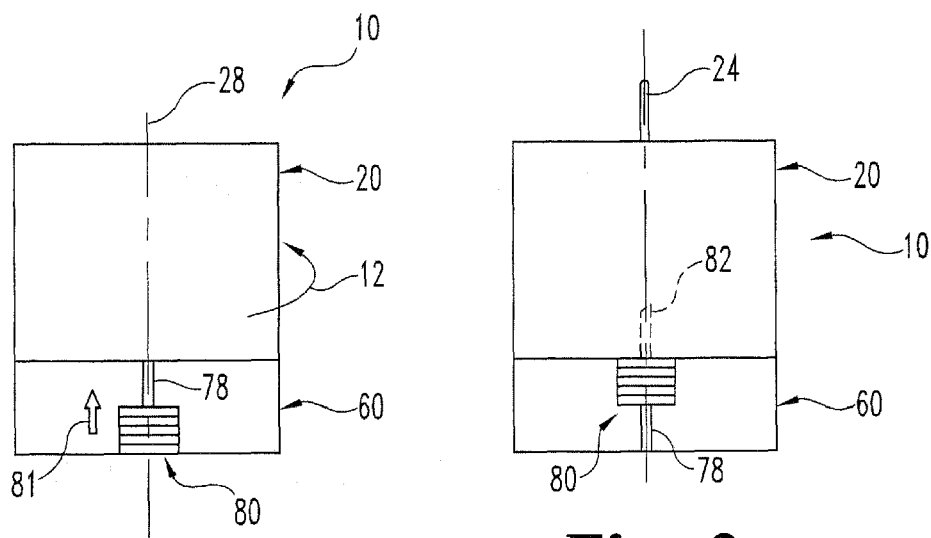
Fig. 1
Fig. 2
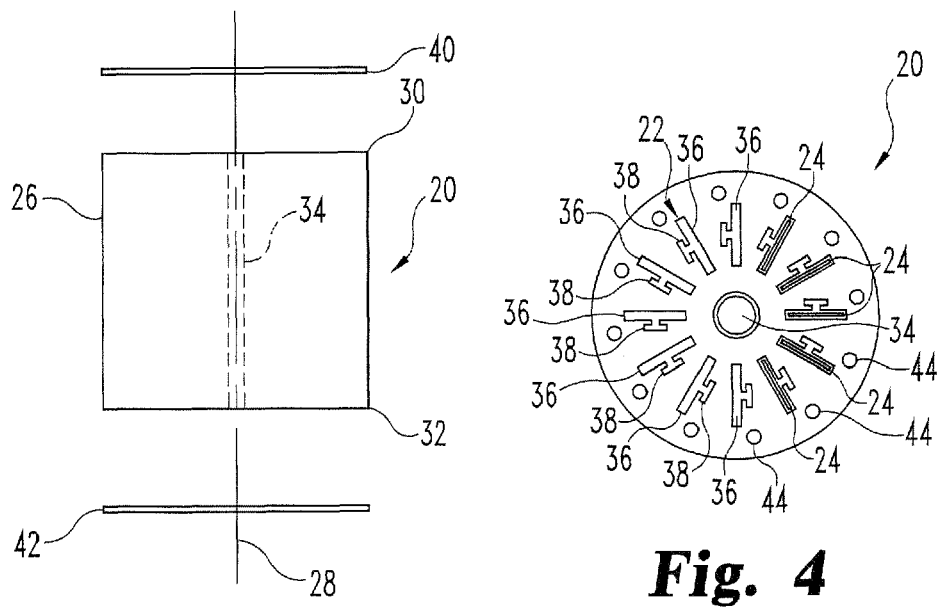
Fig. 3
Fig. 4

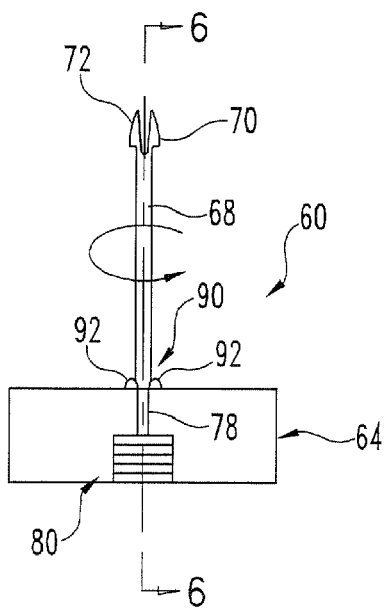
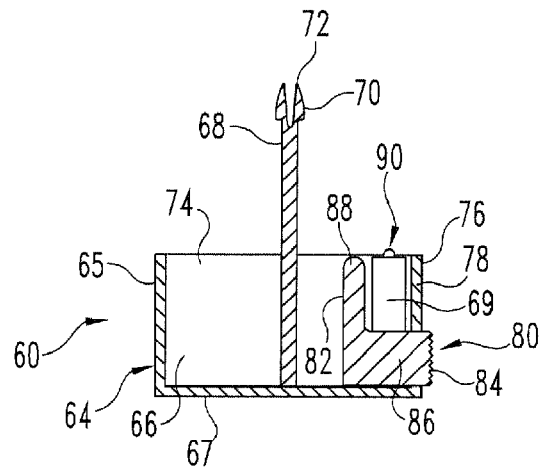
Fig. 5
Fig. 6
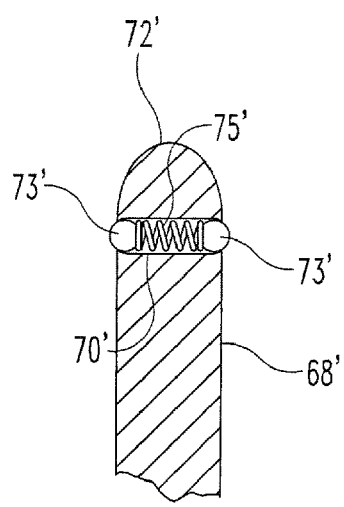
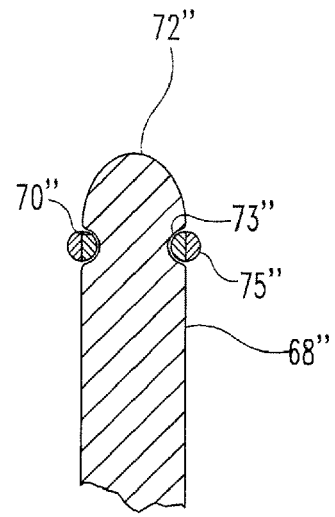
Fig. 7
Fig. 8

BIOSENSOR ASSEMBLY WITH DRUM TYPE CONTAINER FOR ANALYTICAL ELEMENTS

CROSS REFERENCE TO RELATED APPLICATIONS

This application is a divisional of U.S. patent application Ser. No. 12/324,088 filed on Nov. 26, 2008, now U.S. Pat. No. 8,147,755 which is incorporated herein by reference in its entirety.

FIELD OF THE INVENTION

This application relates to an improved container, particularly a drum type container for analytical elements, such as blood glucose test strips.

BACKGROUND

As the number of patients suffering from diabetes and similar medical conditions increases, self-monitoring of blood glucose wherein the patient monitors his or her blood glucose levels has become a common practice. The purpose of monitoring the blood-glucose level is to determine the concentration level and then to take corrective action, based upon whether the level is too high or too low, to bring the level back within a normal range. The failure to take corrective action can have serious medical implications. Glucose monitoring is a fact of everyday life for diabetic individuals, and the accuracy of such monitoring can literally mean the difference between life and death. Failure to test blood glucose levels accurately and on a regular basis can result in serious diabetes-related complications, including cardiovascular disease, kidney disease, nerve damage and blindness.

People with diabetes who intensively manage their blood sugar experience long-lasting benefits. The Diabetes Control and Complications Trial (DCCT) was a clinical study conducted from 1983 to 1993 by the National Institute of Diabetes and Digestive and Kidney Diseases (NIDDK). The DCCT compared intensive to conventional treatments. Patients on intensive treatment kept glucose levels as close to normal as possible with at least three insulin injections a day or an insulin pump, and frequent self-monitoring of blood glucose. Intensive treatment aimed to keep hemoglobin A1c (HbA1c), which reflects average blood glucose over a 2- to 3-month period, as close to normal as possible. Conventional treatment consisted of one or two insulin injections a day with once-a-day urine or blood glucose testing. The results of the DCCT study showed that keeping blood glucose levels as close to normal as possible slows the onset and progression of eye, kidney, and nerve diseases caused by diabetes. In fact, it demonstrated that any sustained lowering of blood glucose helps, even if the person has a history of poor control.

A number of glucose meters are currently available that permit an individual to test the glucose level in a small sample of blood. Many of the meter designs currently available make use of a disposable test strip which in combination with the meter measures the amount of glucose in the blood sample electrochemically. Storage of test strips is necessary in order for the patient to take several readings throughout the day to monitor blood glucose levels. Maintaining the integrity of the stored test strips is important to assure accuracy of the glucose measurements. Ready and easy access to a stored test strip can promote frequent monitoring by the user. Given the ramifications of accurate and frequent monitoring, improvements in the apparatus and/or procedures to meter blood glucose are desired.

SUMMARY

In one embodiment of the present invention there is a drum type container for analytical elements. The container comprises a casing defining a compartment with a plurality of portions for receiving respective ones of a plurality of glucose test strips. The container comprises a base assembly to which the casing is rotatably mounted. The base assembly includes a means for dispensing the glucose test strips from the casing and means for maintaining an alignment of a selected one of the compartment portions with the dispensing means.

In another embodiment of the present invention there a drum type casing extending along a longitudinal axis between a first end and an opposite second end. The casing defines a plurality of compartment portions extending along the longitudinal axis between the first and second ends for receiving respective ones of a plurality of analytical elements. The casing further includes a number of detents radially spaced about the longitudinal axis that extend into the second end in the direction of the longitudinal axis. A base assembly is mounted to the second end of the casing so that the casing is rotatable relative to the base assembly about the longitudinal axis. The base assembly includes a dispenser mechanism movable between the base assembly and the casing to dispense an analytical element from the respective compartment portion and a locking mechanism releasably engaged to at least one of the detents when the at least one detent is aligned with the locking mechanism. The detents and the locking mechanism are arranged so that the locking mechanism normally projects from the base assembly along the longitudinal axis to engage at least one of the detents and maintain the base assembly and the casing in position relative to one another with the dispenser mechanism aligned with one of the plurality of compartment portions. At least a portion of the dispenser mechanism is movable through the second end of the casing to contact the analytical element in the aligned compartment portion to displace the analytical element through the first end of the casing.

In one refinement of the embodiment the casing includes a first sealing member at the first end and a second sealing member at the second end, the second sealing member being configured for penetration by the dispenser mechanism to displace the analytical element therein through the first sealing member while the first and second sealing member maintain remaining ones of the plurality of compartments housing analytical elements in an airtight condition.

In another refinement of the embodiment, the base assembly includes a body extending from the second end of the casing, the body including a cavity housing at least a portion of the dispenser mechanism.

In another refinement of the embodiment, the dispenser mechanism includes an actuator mounted to the body with the actuator accessible outside the cavity and a plunger in the cavity coupled to the actuator. The plunger is movable with the actuator from a first position where an upper end of the plunger is located within the cavity to a second position where the upper end extends through the second sealing member into the aligned compartment portion.

In another refinement of the embodiment, the body of the base assembly includes a side wall extending around the cavity and an end wall opposite the casing, the body further including a longitudinal slot extending through the side wall and opening into the cavity. The actuator extends through the slot and is coupled to the plunger and portions of the side wall along the slot frictionally engage the actuator to maintain the plunger in the first position until sufficient force is applied to the actuator to overcome the frictional engagement to move the actuator along the slot and the plunger to the second position.

In another refinement of the embodiment, the casing further includes a plurality of desiccant compartments, each of the desiccant compartments being located adjacent to and in communication with a respective one of the plurality of compartment portions.

In another refinement of the embodiment, the base assembly includes a spindle extending along the longitudinal axis and the casing includes a bore along the longitudinal axis for receiving the spindle therein so that the casing is rotatable relative to the base assembly about the spindle.

In another refinement of the embodiment, the locking mechanism includes a locking member housed in a receptacle in the base assembly and a spring in the receptacle normally biases the locking member in the direction of the longitudinal axis toward the second end of the casing to engage a corresponding one of the detents when the corresponding detent is aligned with the locking member.

In another refinement of the embodiment, the locking mechanism includes a first locking member housed in a first receptacle in the base assembly, a first spring in the first receptacle normally biasing the first locking member toward the second end of the casing, a second locking member housed in a second receptacle in the base assembly, and a second spring in the second receptacle normally biasing the second locking member toward the second end of the casing. The first and second locking members and the number of detents are arranged so that the first and second locking members engage respective ones of first and second detents located on generally opposite sides of the aligned compartment portion when the first and second detents are aligned with the first and second locking members.

In another refinement of the embodiment, the casing is disposable and the base assembly is reusable.

In another embodiment of the present invention there is a container comprising a plurality of analytical elements and a drum type casing extending along a longitudinal axis between a first end and an opposite second end, the casing defining a plurality of compartment portions extending along the longitudinal axis between the first and second ends for receiving respective ones of the plurality of analytical elements. The casing also includes a number of detents radially spaced about the longitudinal axis that extend into the second end in the direction of the longitudinal axis. The container further includes a base assembly mounted to the second end of the casing so that the casing is rotatable relative to the base assembly about the longitudinal axis. The base assembly includes dispenser means for dispensing an analytical element from the respective compartment portion and locking means confined within the base assembly and the casing for engaging at least one of the detents when the at least one detent is aligned with the locking means. The detents and the locking means are arranged so that the locking means engage the at least one detent in the second end to maintain the base assembly and the casing in position relative to one another with the dispenser means aligned with one of the plurality of compartment portions. The dispenser means is movable through the second end of the casing to contact the analytical element in the aligned compartment portion to displace the analytical element through the first end of the casing.

In one refinement of the embodiment, the casing includes a first sealing member at the first end and a second sealing member at the second end, the second sealing member being configured for penetration by the dispenser mechanism to displace the analytical element therein through the first sealing member while maintaining remaining ones of the plurality of compartments housing analytical elements in an airtight condition and the second sealing member is arranged in non-overlapping relation to the plurality of detents in the second end of the casing.

In another refinement of the embodiment, the dispenser means includes an actuator mounted along the base assembly outside the base assembly and a plunger in the base assembly coupled to the actuator. The plunger is movable with the actuator from a first position where an upper end of the plunger is located within the base assembly to a second position where the upper end extends into the aligned compartment portion to displace the analytical element in the aligned compartment portion through the first end of the casing.

In another refinement of the embodiment, the locking means includes a locking member housed in a receptacle within the base assembly and a spring in the receptacle normally biasing the locking member in the direction of the longitudinal axis toward the second end of the casing to engage a corresponding one of the detents when the corresponding detent is aligned with the locking member.

In another refinement of the embodiment, the locking means includes a first locking member housed in a first receptacle within the base assembly, a first spring in the first receptacle normally biasing the first locking member in the direction of the longitudinal axis toward the second end of the casing, a second locking member housed in a second receptacle within the base assembly, and a second spring in the second receptacle normally biasing the second locking member in the direction of the longitudinal axis toward the second end of the casing. The first and second locking members and the number of detents are arranged so that the first and second locking members engage respective ones of first and second detents located on generally opposite sides of the aligned compartment portion when the first and second detents are aligned with the first and second locking members.

In another refinement of the embodiment, the base assembly includes a side wall extending around a cavity and an end wall opposite the casing, the body further including a longitudinal slot extending through the side wall and opening into the cavity. The dispensing means include an actuator outside the cavity adjacent the slot, a connector extending through the slot to a plunger within the cavity, the plunger including an upper end and having a first position where the upper end is positioned in the cavity and the actuator is movable along the slot to displace the plunger to a second position so that the upper end extends from the cavity through the second of the casing into the aligned compartment portion to displace the respective analytical element through the first end of the casing. The first and second locking members are located adjacent to and on generally opposite sides of the longitudinal slot.

In another embodiment of the present invention, a container comprises a plurality of analytical elements and a drum type casing extending along a longitudinal axis between a first end and an opposite second end. The casing includes a plurality of compartment portions extending along the longitudinal axis between the first and second ends with each of the plurality of analytical elements positioned in a respective one of the plurality of compartment portions. The casing also includes a number of detents radially spaced about the longitudinal axis that extend into the second end in the direction of the longitudinal axis. The container further includes a first sealing member engaged to the first end of the casing and a second sealing member engaged to the second end of the casing, the first and second sealing members sealing the plurality of analytical elements in the plurality of compartments.

A base assembly is rotatably mounted to the second end of the casing with the base assembly and the casing rotatable relative to one another about the longitudinal axis to align a selected one of the compartment portions in a location relative to the base assembly. The base assembly includes a locking mechanism with a locking member biased in the direction of the longitudinal axis toward the second end of the casing to normally engage at least one of the detents when the selected compartment portion is in the location relative to the base assembly. The locking member is biased to resist rotation of the casing relative to the base assembly until sufficient force is applied by rotating the casing relative to the base assembly about the longitudinal axis to overcome the bias of the locking member. The container further includes a dispenser mechanism including a plunger movable through the second sealing member to contact the analytical element in the selected compartment portion and produce the analytical element from the selected compartment portion through the first sealing member.

In one refinement of the embodiment, the second sealing member is arranged in non-overlapping relation to the number of detents of the casing.

In another refinement of the embodiment, the locking mechanism includes a first locking member housed in a first receptacle within the base assembly, a first spring in the first receptacle normally biasing the first locking member in the direction of the longitudinal axis toward the second end of the casing, a second locking member housed in a second receptacle within the base assembly, and a second spring in the second receptacle normally biasing the second locking member in the direction of the longitudinal axis toward the second end of the casing. The first and second locking members and the number of detents are arranged so that the first and second locking members engage respective ones of first and second detents located on generally opposite sides of the aligned compartment when the first and second detents are aligned with the first and second locking members.

In another refinement of the embodiment, the base assembly includes a body with a side wall extending around a cavity and an end wall opposite the casing. The body further includes a longitudinal slot extending through the side wall and opening into the cavity. The dispenser mechanism includes an actuator outside the cavity adjacent the slot, a connector extending through the slot to the plunger within the cavity, with the plunger including an upper end and having a first position where the upper end is positioned in the cavity and the actuator is movable along the slot to displace the plunger to a second position where the upper end extends from the cavity through the second sealing member into the selected compartment portion of the casing. The first and second locking members are located adjacent to the longitudinal slot on generally opposite sides of the longitudinal slot.

In another refinement of the embodiment, the base assembly includes a spindle extending along the longitudinal axis and the casing includes a bore along the longitudinal axis for receiving the spindle therein so that the casing is rotatable about the spindle.

In another embodiment of the present invention, a biosensor assembly includes a blood glucose meter and an elongated cylindrical container including a casing housing respective ones of a plurality of analytical elements. The meter includes a body with a display and a user interface on a front side of the body. The front side extends between opposite sidewalls of the body and opposite first and second ends of the body. The first end including a port for receiving an analytical element and the second end includes a receptacle extending across the first end. The receptacle opens at each of the opposite sidewalls and the body includes at least one groove in the receptacle extending into the body. The casing is removably mounted to a base assembly extending from the casing along a longitudinal axis of the container. The casing includes at least one tongue extending from an outer surface thereof that is received in the groove in the body of the blood glucose meter. The at least one tongue engages the at least one groove to rotatably fix the casing to the body while allowing the base assembly to rotate relative to the casing about the longitudinal axis to align the dispenser mechanism with a selected one of the plurality of compartment portions.

In one refinement of the embodiment, the at least one tongue extends from the casing along the longitudinal axis of the container.

In another refinement of the embodiment, the at least one tongue includes a pair of tongues that are spaced from one another along the longitudinal axis of the casing and the pair of tongues extend in a direction around the longitudinal axis about the casing. The at least one groove includes a pair of grooves in the receptacle sized and spaced to receive respective ones of the pair of tongues.

In another embodiment of the present invention, a biosensor assembly comprises a blood glucose meter, a container housing a plurality of analytical elements, and a cradle. The blood glucose meter includes a body with a display and a user interface on a front side of the body. The front side extends between opposite sidewalls of the body and opposite first and second ends of the body. The first end includes a port for receiving an analytical element. The cradle includes a U-shaped body that defines an end opening receiving the blood glucose meter and a receptacle opposite the end opening. The U-shaped body includes an end wall extending around the receptacle that includes a window opening into the receptacle. The container includes an elongated cylindrical casing with a plurality of compartment portions housing respective ones of the plurality of analytical elements. The casing is removably mounted to a base assembly to extend from the base assembly along a longitudinal axis. The casing is received in the receptacle of the cradle with a sidewall of the casing adjacent to the window and with the base assembly engaged by the U-shaped body to rotatably fix the base assembly relative to the cradle while allowing the casing to rotate relative to the base assembly about the longitudinal axis to align the dispenser mechanism with a selected one of the plurality of compartment portions.

In another embodiment of the present invention, a container comprises casing with a plurality of analytical elements and a base assembly that is mountable to the second end of the casing with the base assembly and the casing rotatable relative to one another to align a selected one of the compartment portions in a location relative to the base assembly. The casing is a disposable component that is discarded when the analytical elements housed therein are used, and the base assembly is re-usable after the casing is discarded. Casings are separately available that include new, unused analytical elements for mounting to and dispensing by the reusable base assembly.

BRIEF DESCRIPTION OF THE FIGURES

FIG. 1 is an elevation view of a drum type container for analytical elements according to one embodiment of the present invention.

FIG. 2 is an elevation view of the container of FIG. 1 with the dispenser mechanism actuated.

FIG. 3 is an exploded elevation view of a casing of the container of FIG. 1.

FIG. 4 is a bottom plan view of the end of the housing of the casing of FIG. 3 looking along its longitudinal axis.

FIG. 5 is an elevation view of a base assembly of the container of FIG. 1.

FIG. 6 is a section view of the base assembly through line 6-6 of FIG. 5.

FIG. 7 is a partial view in section of another embodiment spindle.

FIG. 8 is a partial view in section of another embodiment spindle.

DETAILED DESCRIPTION OF THE ILLUSTRATED EMBODIMENTS

Figure 9A:
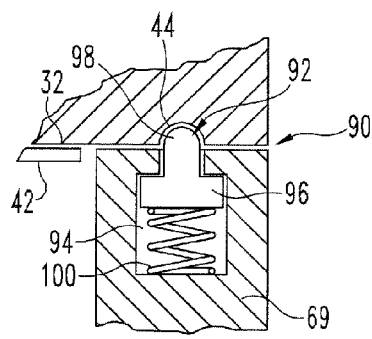
FIG. 9A is a side elevation view in partial section of a locking mechanism of the base assembly of FIG. 5 in an engaged position with the casing of the container.

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Existing test strips for glucose monitoring are available in a variety of packaging. Various embodiments of the present invention relate to an easy to use primary drum type container for blood glucose strips. In one embodiment, the drum type container may be used as a stand-alone container and dispensing system for test strips such that it is not mounted or otherwise associated with the blood glucose meter. Examples of drum type containers are provided in U.S. Patent Application No. 2007/0009381 to Schulat et al. and U.S. Pat. No. 6,497,845 to Sacherer, each of which is incorporated herein by reference in its entirety. In other embodiments, the drum type container is mounted with a blood glucose meter, as discussed further below.

With reference to FIGS. 1-9B there is illustrated one embodiment of the present invention of a drum type container 10 that may be mounted on a meter or used as a stand alone device. Container 10 may be described herein as containing and dispensing glucose test strips. However, the container might contain and dispense other analytical elements. Container 10 includes a casing 20 that defines an internal compartment 22. The internal compartment 22 includes a plurality of compartment portions 36 each sized and configured to receive at least one analytical element 24, such as blood glucose test strips. Casing 20 is mounted to a base assembly 60. A sliding dispenser mechanism 80 translates as indicated by arrow 81 to cause the container 10 to eject an analytical element 24 from a selected one of the portions 36 of compartment 22, such as shown in FIG. 2. Casing 20 is rotatable on base assembly 60 about a longitudinal axis 28 of container 10, as indicated by arrow 12 of FIG. 1, in order to align dispenser mechanism 80 with another portion of compartment 22 that houses another analytical element 24 for subsequent dispensing.

Referring to FIGS. 3-4, casing 20 is shown to include an elongated, cylindrical housing 26 extending along longitudinal axis 28 between a first end 30 and an opposite second end 32. Housing 26 defines a central bore 34 centered along longitudinal axis 28 that extends between first end 30 and second end 32. Bore 34 opens at least at second end 32.

As shown in FIG. 4, housing 26 includes a circular shape orthogonally to longitudinal axis 28. Housing 26 defines internal compartment 22 for housing a number of analytical elements 24. Compartment 22 may include a plurality of separate compartment portions 36 extending along the length of housing 26. Each of compartment portions 36 opens at each of first and second ends 30, 32 of housing 26. A separate analytical element 24 can be positioned in each of the compartment portions 36. Only a few of compartment portions 36 are shown with an analytical element 24 in FIG. 4 for illustrative purposes, it being understood that all compartment portions 36 typically house an analytical element 24 before initial use of container 10. In one embodiment, each of the compartment portions 36 is connected to a respective desiccant chamber 38. Each desiccant chamber 38 is in communication with it respective compartment portion 36 via an airway that extends between and opens in desiccant chamber 38 and compartment portion 36. Each desiccant chamber 38 houses a desiccant to control moisture in the respective connected compartment portion 36 to preserve the integrity of the analytical element 24 housed in the compartment portion 36. Other configurations for compartment portions 36 and desiccant chambers are within the ordinary skill in the art and are not elaborated upon here.

Casing 20 also includes a first sealing member 40 connected at first end 30 of housing 26 and a second sealing member 42 connected at second end 32 of housing 26. Sealing members 40, 42 provide a seal that prevents moisture and other containments from entering the compartment portions 36, and provide a hermetic seal to isolate the analytical elements 24 from the environment. In one embodiment, sealing members 40, 42 are made from sealable foil that is about 0.001 inches thick with a heat sealable coating. The sealable foil is applied to each end 30, 32 of housing 26 with analytical elements 24 in compartment portions 36. Sealing members 40, 42 are sealed with the end wall portions of housing 26 located between and around compartment portions 36 so that each of the compartment portions is sealed individually and separately from the other compartment portions 36. Thus, if one of sealing members 40, 42 is punctured at one of the compartment portions 36, the remaining compartment portions remain sealed from the environment by sealing members 40, 42. Other embodiments contemplate other forms and materials for sealing members 40, 42. For example, each of the compartment portions 36 can be provided with a separate lid, valve, or cap over its respective end openings.

As discussed further below, housing 26 includes a number of detents 44 (only a few of which are designated with reference numeral 44 in FIG. 4) formed in second end 32 of housing 26. Detents 44 are spaced uniformly and radially about longitudinal axis 28 and in the illustrated embodiment are located adjacent to the circumferential edge of housing 26. Each of the detents 44 is positioned between adjacent ones of respective compartment portions 36. Detents 44 extend into and are recessed in the end surface of body 26 at second end 32 in the direction of longitudinal axis 28.

Referring to FIGS. 5 and 6, base assembly 60 will be further discussed. Base assembly 60 includes a cylindrical body 64 with a side wall 65 and end wall 67 that define a cavity 66. As used herein, the term upper refers to the end or direction of base assembly 60 oriented toward casing 20, and not necessarily to the orientation of container 10 when held or used by the user. Side wall 65 extends from end wall 67 to an upper end 74 where cavity 66 opens. In one embodiment, a spindle 68 is centered in body 64 and extends in cavity 66 from end wall 67 to an outer end 72 that projects from upper end 74 of body 64. Spindle 68 is sized for positioning in bore 34 of housing 26, and extends along longitudinal axis 28 of container 10 when housing 26 is positioned on spindle 68. Housing 26 is rotatable about spindle 68 to align a selected one of compartment portions 36 with dispenser mechanism 80. Spindle 68 includes a resilient or molded flange 70 extending therefrom adjacent to outer end 72. Flange 70 flexes to permit placement of housing 26 about spindle 68 with lower end 32 of housing 26 and sealing member 42 adjacent to and supported by upper end 74 of body 64, as shown in FIGS. 1 and 2. Flange 70 frictionally maintains the axial position of casing 20 relative to base assembly 60, yet permits removal when sufficient force is applied along longitudinal axis 28 to separate base assembly 60 and casing 20 by overcoming the resistance supplied by flange 70.

Referring now to FIGS. 7 and 8, there are shown other embodiments of spindle 68 for securing housing 26 on base assembly 60. In FIG. 7, spindle 68' includes an upper end 72' having spring-loaded pins 73' adjacent thereto. Pins 73' are located in and captured in a receptacle 70' adjacent upper end 72'. A spring or biasing member 75' is located in receptacle 70' and contacts pins 73' to normally bias pins 73' outwardly from receptacle 70'. Pins 73' move into receptacle 70' as housing 26 is moved along spindle 68' until pins 73' align with a groove, recess, detent or other structure in bore 34 of housing 26. Spring 75' biases pins 73' to normally engage housing 26 and axially retain it on spindle 68' until sufficient axial force is applied to housing 26 to overcome the bias of pins 73' and allow housing 26 to be axially removed from spindle 68'.

In FIG. 8, spindle 68" includes an upper end 72" having a circumferential groove 70" formed therearound. A spring-loaded collar 73" is located in and normally captured in groove 70". A spring or biasing member 75" is located around the central opening of collar 73" and nominal contacts spindle 68" in groove 70". The outer perimeter of collar 73" is received in a groove or notch in bore 34 of housing 26 to axially secure housing 26 and spindle 68" to one another. Spring 75" is biased to normally engage spindle 68" and axially secure housing 26 thereon until sufficient axial force is applied to withdraw spindle 68" by outwardly expanding spring 75" and overcome its bias to allow housing 26 to be axially removed from spindle 68".

Side wall 65 of body 64 includes a slotted opening 78 (also see FIGS. 1 and 2) extending therethrough along one side of body 64. Dispenser mechanism 80 is mounted in and extends through slotted opening 78. Dispenser mechanism 80 includes a plunger 82 in cavity 66 and an actuator 84 along body 64 outside cavity 66. Actuator 84 and plunger 82 are linked to one another by a connector 86 extending through opening 78. The portions 76 of side wall 65 surrounding slotted opening 78 can frictionally engage actuator 84 and/or connector 86 to maintain the selected positioning of plunger 82 relative to body 64 and casing 20. In FIGS. 1 and 6, dispenser mechanism 80 is shown in a retracted position where plunger 82 is recessed below upper end 74 of base assembly 60 so that sealing member 42 is not penetrated when casing 20 is mounted to base assembly 60. In other embodiments, actuator 84 is spring-biased to normally maintain plunger 82 in the retracted position shown in FIGS. 1 and 6, or there is provided a catch or latch to maintain the selected positioning of actuator 84 and plunger 82.

Actuator 84 is readily accessibly by the user to move plunger 82 relative to body 64 toward and away from second end 32 of casing 20. When it is desired to dispense an analytical element 24 from its respective compartment portion 36, the user slides or moves actuator 84 along slotted opening 78 toward casing 20, which in turn advances an upper end 88 of plunger 82 through sealing member 42 and into the aligned compartment portion 36 housing the desired analytical element 24. Upper end 88 of plunger 82 engages the lower end of the analytical element 24 and pushes the upper end of the analytical element 24 through sealing member 40 at first end 30 of housing 26. The analytical element 24 is produced out of its respective compartment portion 36 so it can be pulled from casing 20 by the user, as shown in FIG. 2. Plunger 82 and the produced analytical element 24 only puncture the portions of sealing members 40, 42 sealing the compartment portion 36 in which the produced analytical element 24 was stored, while the remaining compartment portions 36 remain sealed by sealing members 40, 42 unless an analytical element was already produced therefrom.

Figure 9B:
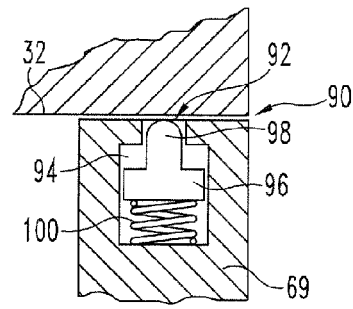
FIG. 9B is the view of FIG. 9A with the locking mechanism in a non-engaged position with the casing of the container.

Referring now to FIGS. 9A and 9B, there are shown additional features of one embodiment of a locking mechanism 90 that interacts with aligned ones of the detents 44 to maintain a selected and aligned positioning of casing 20 relative to base assembly 60. Locking mechanism 90 includes at least one locking member 92 housed in a receptacle 94 of body 64 located in a support member 69 in cavity 66. Locking member 92 includes a base portion 96 and an upper portion 98. Base portion 96 is captured in receptacle 94, and a biasing member 100 in receptacle 94 normally biases locking member 92 outwardly so that upper extension 98 projects outwardly from upper end 74 of body 64. In the locking position shown in FIG. 9A, upper portion 98 of locking member 92 is received in and biased into an aligned one of the detents 44. The engagement between locking member 92 and detent 44 securely maintains the rotational positioning of casing 20 on base assembly 60 with plunger 82 aligned with one of the compartment portions 36 for subsequent ejection of an analytical element 24 via movement of actuator 84.

After removal of the analytical element 24, casing 20 can be rotated as indicated by arrow 12 in FIG. 1 about longitudinal axis 28 relative to base assembly 60. This rotational force and the rounded interface between detent 44 and locking member 92 pushes locking member 92 against spring 100 and into receptacle 94, as shown in FIG. 9B. This allows rotation of casing 20 until the next adjacent detent 44 is aligned with locking member 92. Spring 100 then forces locking member 92 into the next aligned detent 44 and secures casing 20 in a rotationally selected position relative to base assembly 60 with plunger 82 aligned with the next adjacent compartment portion 36. In one embodiment, it is contemplated that sealing member 42 is configured and sized relative to housing 26 so that detents 44 are not covered or obstructed by sealing member 42, such as shown in FIG. 9A. This allows direct contact between the material comprising housing 26 and locking member 92. In another embodiment, it is contemplated that sealing member 42 is punctured or deformed by locking member 92 by the biasing force of spring 100 so that locking member 92 is sufficiently received in detent 44 to maintain the selected rotational position.

As shown in FIG. 5, it is contemplated that locking mechanism 90 can be provided with one locking member 92 on each side of slotted opening 78. The dual locking members 92 associated with this embodiment of locking mechanism 90 simultaneously engage the respective detents 44 located on each side of the selected compartment portion 36 aligned with plunger 82. The dual locking members 92 can increase resistance to rotation of casing 20 relative to base assembly 60 until sufficient rotational force is applied to overcome the resistance supplied by each locking member 92 and its respective biasing member 100. Other embodiments contemplate more than two locking members are provided to engage more than two detents 44. In yet other embodiment, locking mechanism 90 includes a single locking member 92.

By providing the interface of locking mechanism 90 with casing 20 on the end of casing 20, the overall profile of container 10 is minimized. Other than actuator 84, the moving parts of dispenser mechanism 80 and locking mechanism 90 are confined within container 10, minimizing the potential for damage or tampering. As used herein in association with locking mechanism 90, "confined within" means that locking mechanism 90 is housed and located entirely within container 10 and is not accessible by the user or other persons or external elements against which container 10 may be positioned unless container 10 is disassembled. Other embodiments of container 10 contemplate arrangements where the locking mechanism 90 is not confined within container 10.

It is contemplated that locking members 92 include a spherical upper end to facilitate rotation of casing 20 when sufficient force is applied thereto to displace locking member 92 against the bias of spring 100 when it is received in a detent 44. In the illustrated embodiment, locking member 92 includes a cylindrical body extending between its upper portion 98 and base portion 96. Other embodiments contemplate that base portion 96 and upper portion 98 form a sphere. Base portion 96 can be retained within receptacle 94 with a C-shaped retaining member, a lip, or other structure at the upper end of receptacle 94 to prevent passage of base portion 96 therethrough.

In one embodiment, casing 20 is a disposable portion of container 10 and base assembly 60 is a reusable portion of container 10. The user can initially purchase a container 10 that includes both base assembly 60 and a sealed casing 20 housing analytical elements, or can purchase base assembly 60 and casing 20 separately. Additional sealed casings can be purchased as re-fills. When the analytical elements in the casing 20 in use are depleted, the empty casing 20 is discarded. A new sealed casing 20 housing analytical elements is then secured to the re-usable base assembly 60.

Figure 10A:
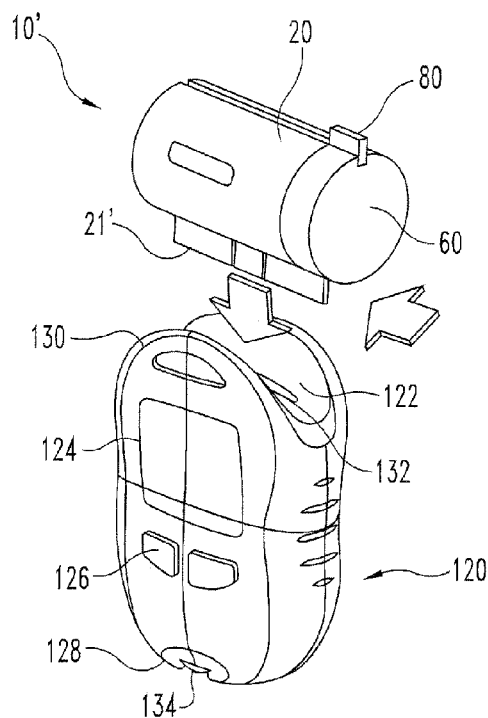
FIG. 10A is an exploded perspective view of a biosensor device and another embodiment container for housing analytical elements that is attachable to the biosensor device.

The drum type container can be removably mounted to a biosensor device, such a blood glucose meter, so that the analytical elements are selectively dispensed from the container for ready access and use. FIG. 10A shows one embodiment of a blood glucose meter 120. Meter 120 is shown with a display 124 and a user interface 126 on a front side thereof. Meter 120 extends between opposite ends 128, 130. One of the ends 128, 130, such as end 128 in the illustrated embodiment, includes a port 134 with circuitry to measure one or more properties of a bodily fluid placed on the analytical element dispensed from container 10' when positioned in port 134. The other of the ends 128, 130, such as end 130 in the illustrated embodiment, includes a receptacle 122 for removably receiving container 10'.

Figure 10B:
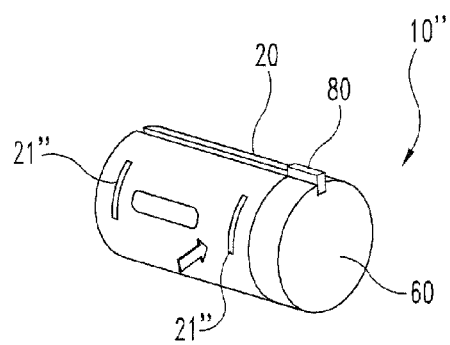
FIG. 10B is a perspective view of another embodiment container removably attachable to a biosensor device.

Container 10' is like container 10 discussed above and includes a casing 20 for housing analytical elements and a base assembly 60 to which casing 20 is removably mounted. However, container 10' also includes a rail or tongue 21' extending from casing 20 and longitudinally along longitudinal axis 28. Tongue 21' is received in a groove 132 in receptacle 122 of meter 120. Tongue 21' and groove 132 interact with one another to prevent casing 20 from rotating relative to meter 120, but allow base assembly 60 to rotate relative to casing 20 to align dispensing mechanism 80 with the selected compartment portion 36 to dispense an analytical element 24 from the selected compartment portion. In one embodiment, tongue 21' includes a ROM key or other identifier therewith so that when tongue 21' is inserted in meter 120 information, such as calibration and other data regarding the analytical element housed in casing 20, is automatically downloaded to meter 120. FIG. 10B shows another embodiment container 10" that is similar to container 10' discussed above. However, container 10" includes a pair of rails or tongues 21" extending partially therearound about longitudinal axis 28 and on an outer surface of casing 20. Rails 21" are received in correspondingly sized, shaped and spaced grooves (not shown) formed in receptacle 122 of meter 120. In either embodiment of FIG. 10A or 10B, when casing 20 is depleted of analytical elements, container 10', 10" can be removed from meter 120 and the depleted casing 20 removed from base assembly 60 for disposal of casing 20. A new casing 20 can then be mounted to base assembly 60, and the assembled container 10', 10" re-attached to meter 120 for use in storing and dispensing analytical elements.

Figure 11A:
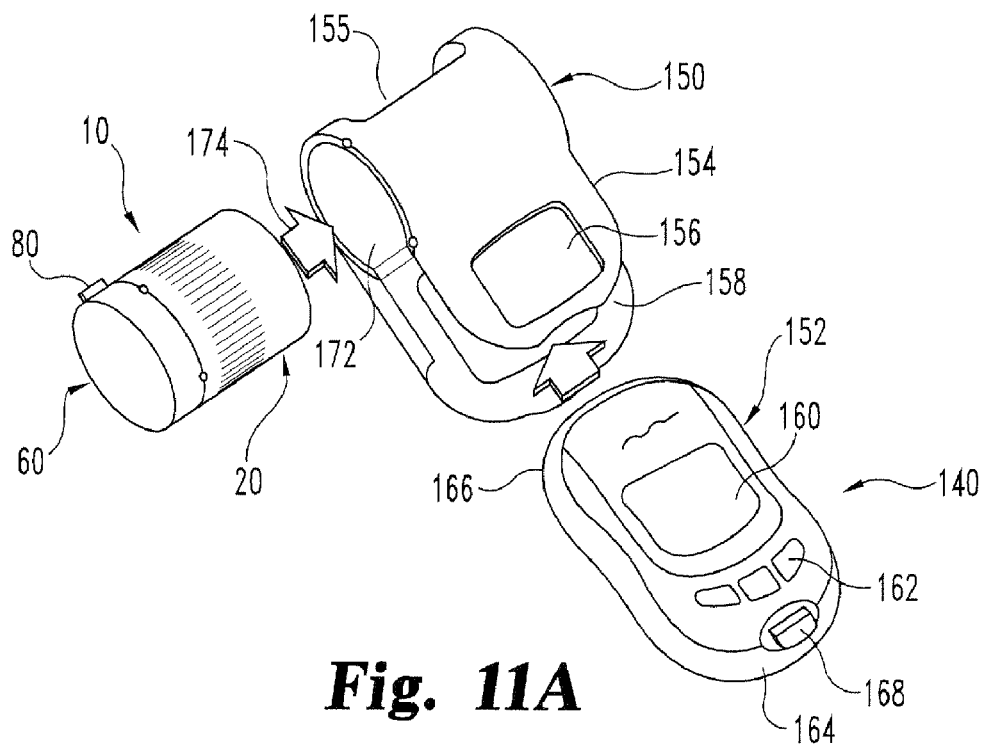
FIG. 11A is an exploded perspective view of a cradle for removably receiving another embodiment biosensor device and container for housing analytical elements.
Figure 11B:
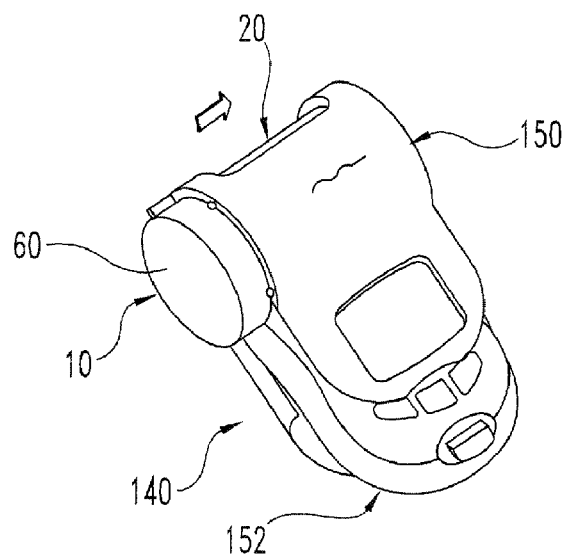
FIG. 11B is a perspective view of the assembled cradle, biosensor device and container of FIG. 11A.

FIGS. 11A-11B show another embodiment of a biosensor assembly 140 that includes a cradle 150, a container 10, and a blood glucose meter 152. Meter 152 is shown with a display 160 and a user interface 162 on a front side thereof. Meter 152 extends between opposite ends 164, 166. One of the ends 164, 166, such as end 164 in the illustrated embodiment, includes a port 168 with circuitry to measure one or more properties of a bodily fluid deposited on an analytical element dispensed from container 10 when inserted in port 168. The other of the ends, such as end 166 in the illustrated embodiment, is sized for positioning through end opening 158 of cradle 150.

Cradle 150 includes a U-shaped body having opening 158 at one end thereof and a receptacle 172 at the end thereof opposite end opening 158. Receptacle 172 is sized to receiver container 10 therein along path 174, as shown in FIG. 11B. When assembled, meter 152 resides between the walls of U-shaped body 154 with display 160 visible through opening 156 of cradle 150. Body 154 engages base assembly 60 to prevent it from rotating relative to cradle 150, while body 154 defines a window 155 that opens into receptacle 172 to provide access to casing 20. The user can access and rotate casing 20 in receptacle 172 through window 155 relative to base assembly 60 to align the selected compartment portion 36 with dispensing mechanism 80 to dispense an analytical element 24 through the end of casing 20. When casing 20 is depleted of analytical elements, container 10 can be removed from cradle 150 and the depleted casing 20 removed from base assembly 60 for disposal of casing 20. A new casing 20 can then be mounted to base assembly 60, and the assembled container 10 re-positioned in receptacle 172 of cradle 150 for subsequent use.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:
1. A biosensor assembly, including:
a blood glucose meter including a body with a display and a user interface on a front side of said body, said front side extending between opposite sidewalls of said body and opposite first and second ends of said body, said first end including a port for receiving an analytical element said meter including circuitry electrically connected to said analytical element when said analytical element is received within said port, said circuitry capable of measuring one or more properties of a fluid on said analytical element, said meter including said display in an electrical connection to display said measurement and said second end including a receptacle extending across said second end, said receptacle opening at each of said opposite sidewalls and said body includes at least one groove in said receptacle extending into said body; and
an elongated cylindrical container including a casing with a plurality of compartment portions housing respective ones of a plurality of analytical elements, said casing being removably mounted to a base assembly extending from said casing along a longitudinal axis of said container, wherein said casing includes at least one tongue extending from an outer surface thereof that is received in said groove in said body of said blood glucose meter, said at least one tongue engaging said at least one groove to rotatably fix said casing to said body while allowing said base assembly to rotate relative to said casing about said longitudinal axis to align a dispenser mechanism of said base assembly with a selected one of said plurality of compartment portions.

2. The assembly of claim 1, wherein said at least one tongue extends from said casing along said longitudinal axis of said container.

3. The assembly of claim 2, wherein said at least one tongue includes a pair of tongues that are spaced from one another along said longitudinal axis of said casing and said pair of tongues extend in a direction around said longitudinal axis about said casing, and said at least one groove includes a pair of grooves in said receptacle sized and spaced to receive respective ones of said pair of tongues.

4. The assembly of claim 1, wherein said casing includes a first sealing member at a first end thereof and a second sealing member at an opposite second end thereof, said second sealing member being configured for penetration by said dispenser mechanism to displace the analytical element therein through said first sealing member while said first and second sealing member maintain remaining ones of said plurality of compartment portions housing analytical elements in an airtight condition.

5. The assembly of claim 4, wherein said base assembly includes:
a body extending from said second end of said casing, said body including a cavity housing at least a portion of said dispenser mechanism.

6. The assembly of claim 5, wherein said dispenser mechanism includes:
an actuator mounted to said body with said actuator accessible outside said cavity; and
a plunger in said cavity coupled to said actuator, wherein said plunger is movable with said actuator from a first position wherein an upper end of said plunger is located within said cavity to a second position wherein said upper end extends through said second sealing member into said aligned compartment portion.

7. The assembly of claim 6, wherein:
said body of said base assembly includes a side wall extending around said cavity and an end wall opposite said casing, said body further including a longitudinal slot extending through said side wall and opening into said cavity;
said actuator extends through said slot and is coupled to said plunger; and
portions of said side wall along said slot frictionally engage said actuator to maintain said plunger in said first position until sufficient force is applied to said actuator to overcome said frictional engagement to move said actuator along said slot and move said plunger to said second position.

8. The assembly of claim 1, wherein said base assembly includes a spindle extending along said longitudinal axis and said casing includes a bore along said longitudinal axis for receiving said spindle therein so that said casing is rotatable relative to said base assembly about said spindle.

9. The assembly of claim 1, wherein:
said casing includes a number of detents radially spaced about the longitudinal axis that extend into an end of said casing in the direction of said longitudinal axis; and
said base assembly includes a locking mechanism releasably engaged to at least one of said detents when said at least one detent is aligned with said locking mechanism.

10. The assembly of claim 9, wherein said detents and said locking mechanism are arranged so that said locking mechanism normally projects from said base assembly along said longitudinal axis to engage at least one of said detents and maintain said base assembly and said casing in position relative to one another with said dispenser mechanism aligned with one of said plurality of compartment portions.

11. A biosensor assembly, including:
a blood glucose meter including a body with a display and a user interface on a front side of said body, said front side extending between opposite sidewalls of said body and opposite first and second ends of said body, said first end including a port for receiving an analytical element said meter including circuitry electrically connected to said analytical element when said analytical element is received within said port, said circuitry capable of measuring one or more properties of a fluid on said analytical element, said meter including said display in an electrical connection to display said measurement;
a cradle including a U-shaped body that defines an end opening receiving said blood glucose meter and a receptacle opposite said end opening, said U-shaped body including an end wall extending around said receptacle, said end wall including a window opening into said receptacle; and
an elongated cylindrical container including a casing with a plurality of compartment portions housing respective ones of a plurality of analytical elements, said casing being removably mounted to a base assembly to extend from said base assembly along a longitudinal axis, wherein said casing is received in said receptacle of said cradle with a sidewall of said casing adjacent to said window and with said base assembly engaged by said U-shaped body to rotatably fix said base assembly relative to said cradle while allowing said casing to rotate relative to said base assembly about said longitudinal axis to align a dispenser mechanism of said base assembly with a selected one of said plurality of compartment portions.

12. The assembly of claim 11, wherein said casing includes a first sealing member at a first end thereof and a second sealing member at an opposite second end thereof, said second sealing member being configured for penetration by said dispenser mechanism to displace the analytical element therein through said first sealing member while said first and second sealing member maintain remaining ones of said plurality of compartment portions housing analytical elements in an airtight condition.

13. The assembly of claim 12, wherein said base assembly includes:
a body extending from said second end of said casing, said body including a cavity housing at least a portion of said dispenser mechanism.

14. The assembly of claim 13, wherein said dispenser mechanism includes:
an actuator mounted to said body with said actuator accessible outside said cavity; and
a plunger in said cavity coupled to said actuator, wherein said plunger is movable with said actuator from a first position wherein an upper end of said plunger is located within said cavity to a second position wherein said upper end extends through said second sealing member into said aligned compartment portion.

15. The assembly of claim 14, wherein:
said body of said base assembly includes a side wall extending around said cavity and an end wall opposite said casing, said body further including a longitudinal slot extending through said side wall and opening into said cavity;
said actuator extends through said slot and is coupled to said plunger; and
portions of said side wall along said slot frictionally engage said actuator to maintain said plunger in said first position until sufficient force is applied to said actuator to overcome said frictional engagement to move said actuator along said slot and move said plunger to said second position.

16. The assembly of claim 11, wherein said base assembly includes a spindle extending along said longitudinal axis and said casing includes a bore along said longitudinal axis for receiving said spindle therein so that said casing is rotatable relative to said base assembly about said spindle.

17. The assembly of claim 11, wherein:
said casing includes a number of detents radially spaced about the longitudinal axis that extend into an end of said casing in the direction of said longitudinal axis; and
said base assembly includes a locking mechanism releasably engaged to at least one of said detents when said at least one detent is aligned with said locking mechanism.

18. The assembly of claim 17, wherein said detents and said locking mechanism are arranged so that said locking mechanism normally projects from said base assembly along said longitudinal axis to engage at least one of said detents and maintain said base assembly and said casing in position relative to one another with said dispenser mechanism aligned with one of said plurality of compartment portions.

19. The assembly of claim 11, wherein said body of said cradle defines an opening between said end opening and said receptacle and said display of said blood glucose meter is aligned with said opening when said container is positioned in said receptacle and said blood glucose meter is positioned in said cradle.

20. A biosensor assembly, including:
a blood glucose meter including a body with a display and a user interface on a front side of said body, said front side extending between opposite sidewalls of said body and opposite first and second ends of said body, said first end including a port for receiving an analytical element said meter including circuitry electrically connected to said analytical element when said analytical element is received within said port, said circuitry capable of measuring one or more properties of a fluid on said analytical element, said meter including said display in an electrical connection to display said measurement and said second end including a receptacle extending across said second end, said receptacle opening at each of said opposite sidewalls; and
an elongated cylindrical container including a casing with a plurality of compartment portions housing respective ones of a plurality of analytical elements, said casing being removably mounted to a base assembly extending from said casing along a longitudinal axis of said container, wherein said casing includes is rotatably fixed to said body of said blood glucose meter in said receptacle, said base assembly being rotatable relative to said casing about said longitudinal axis to align a dispenser mechanism of said base assembly with a selected one of said plurality of compartment portions.

\* \* \* \* \*